United States Patent [19]

Foley

[11] Patent Number: 4,584,144

[45] Date of Patent: Apr. 22, 1986

[54] MONOMERIC THIOLOESTERIFICATION OF 1,3-ALKADIENE

[75] Inventor: Paul Foley, Summit, N.J.

[73] Assignee: Celanese Corporation, New York, N.Y.

[21] Appl. No.: 330,628

[22] Filed: Dec. 14, 1981

[51] Int. Cl.$^4$ .......................................... C07C 153/01
[52] U.S. Cl. .................................................. 558/250
[58] Field of Search .................................. 260/455 R

[56] References Cited

U.S. PATENT DOCUMENTS 3,933,884  1/1976  Knifton ........................... 260/455 R Primary Examiner—Henry R. Jiles
Assistant Examiner—Robert C. Whittenbaugh
Attorney, Agent, or Firm—Depaoli & O'Brien

[57] ABSTRACT

This invention provides a process for monomeric thioloesterification of 1,3-alkadiene in the presence of a catalyst which is a stabilized complex of palladium, tertiary phosphine ligand and thiol compound.

Monomeric thioloesterification of 1,3-butadiene with 1-butanethiol and carbon monoxide in accordance with the present invention process provides a high conversion and selectivity yield of 1-butyl 3-thiolopentenoate product.

28 Claims, No Drawings

MONOMERIC THIOLOESTERIFICATION OF 1,3-ALKADIENE

BACKGROUND OF THE INVENTION

Catalytic carbonylation of olefinic and acetylenic compounds to form oxygenated derivatives with an increased content of carbon atoms is a well-established technology. Various developments and improvements are described in U.S. patents such as U.S. Pat. Nos. 2,768,968; 2,863,911; 2,876,254; 3,040,090; 3,455,989; 3,501,518; 3,507,891; 3,652,655; 3,660,439; 3,700,706; 3,723,486; 3,746,747; 3,755,419; 3,755,421; 3,793,369; 3,856,832; 3,859,319; 3,887,595; 3,906,015; 3,917,677; 3,952,034; 3,992,423; 4,102,920; 4,245,115; 4,246,183; and references cited therein.

Of interest with respect to the present invention is the chemical literature relating to dimeric carbonylation of aliphatic conjugated dienes in the presence of a hydroxylated coreactant and a catalyst complex of a Group VIII noble metal and a Group VA tertiary donor ligand. The dimeric carbonylation reaction is illustrated by the following chemical equation with respect to the interaction of 1,3-butadiene with alkanol:

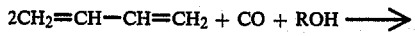

$$2CH_2=CH-CH=CH_2 + CO + ROH \longrightarrow$$

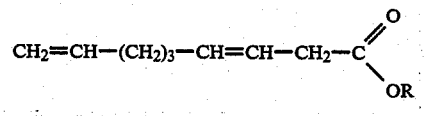

$$CH_2=CH-(CH_2)_3-CH=CH-CH_2-C{\overset{O}{\underset{OR}{\diagdown\!\!\!\!\!\!\!/}}}$$

In a report published in Tetrahedron, 28, 3721 (1972), there is described a dimeric carbonylation of 1,3-butadiene in the presence of alkanol and a palladiumphosphine complex catalyst to yield alkyl 3,8-nonadienoate. The publication discloses that the absence of halide coordinated to the palladium metal is essential for the formation of alkyl nonadienoate product. In the presence of halide, one mole of 1,3-butadiene reacts with one mole of carbon monoxide and one mole of alkanol to yield alkyl 3-pentenoate.

U.S. Pat. No. 4,124,617 describes a process for the selective production of fatty acid derivatives from aliphatic diene substrates, in the presence of dual-function homogeneous palladium complexes and certain classes of organic tertiary nitrogen bases. One aspect of this type of process is that the use of tertiary nitrogen bases promotes the production of various byproducts such as C₅—esters. Another aspect is that the catalyst tends to exhibit a reaction rate decrease during the course of the carbonylation reaction due to instability of the catalyst system.

Also of interest with respect to the present invention is the chemical literature relating to hydroesterification of alpha-olefins to yield alkanoate esters.

In J. Org. Chem., 41, 793(1976) and J. Org., Chem., 41, 2885(1976) there is reported the synthesis of linear carboxylate esters from alpha-olefins in the presence of a homogeneous platinum complex catalyst:

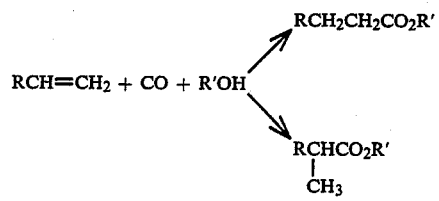

U.S. Pat. No. 3,933,884 describes a process for preparing thioloesters by the interaction of an alpha-olefin with carbon monoxide and a thiol compound in the presence of a catalyst composed of a noble metal halide and a Group IVB metal halide and a Group VB donor ligand.

There is continuing development effort directed to improvement of processes and catalysts for carbonylation and hydroesterification of olefinic substrates to yield oxygenated or sulfurated derivatives of increased carbon content via monomeric and dimeric reaction mechanisms. There has not been any prior art directed specifically to monomeric thioloesterification of 1,3-alkadiene compounds.

Accordingly, it is a main object of this invention to provide an improved process for conversion of aliphatic conjugated dienes into fatty acid derivatives.

It is another object of this invention to provide a process for producing alkyl thioloalkenoate by monomeric thioloesterification of 1,3-alkadiene with high conversion and selectivity to linear product.

It is a further object of this invention to provide a stabilized palladium catalyst system adapted for thioloesterification of olefinic hydrocarbons.

Other objects and advantages of the present invention shall become apparent from the accompanying description and examples.

DESCRIPTION OF THE INVENTION

One or more objects of the present invention are accomplished by the provision of a process for monomeric thioloesterification of 1,3-alkadiene which comprises (1) reacting 1,3-alkadiene with carbon monoxide and thiol compound in a liquid medium containing a stabilized catalyst complex of palladium and tertiary phosphine ligand; and (2) recovering alkyl 3-thioloalkenoate product.

The term "1,3-alkadiene" is meant to include acyclic and cyclic 1,3-diene compounds which contain between about 4–20 carbon atoms, and which can contain other heteroatoms such as oxygen, sulfur, nitrogen and halogen which do not interfere with the invention process thioloesterification. Illustrative of suitable 1,3-alkadiene compounds are 1,3-butadiene; 2-methyl-1,3-butadiene; 2,3-dimethyl-1,3-butadiene; 2-chloro-1,3-butadiene; 1,3-pentadiene; 5-phenyl-1,3-pentadiene; 1,3-hexadiene; 1,3-decadiene; 1,3-cyclopentadiene; 1,3-cyclohexadiene; 1,3-cyclooctadiene; and the like.

The present invention process is particularly adapted for converting a linear 1,3-alkadiene into a monomeric thioloesterification product with a high selectivity ratio of straight chain to branched chain product (e.g., an average ratio of at least 5:1).

Further, under optimal conditions 1,3-butadiene is at least 90 percent converted, and the selectivity to alkyl 3-thioloalkenoate product is at least 90 mole percent, based on the total moles of conversion products.

The term "thiol" is meant to include primary, secondary and tertiary thiol compounds. Illustrative of thiol compounds are those corresponding to the formula:

R—(SH)$_x$ where R is an aliphatic, alicyclic or aromatic substituent containing between about 1–30 carbon atoms, preferably between about 1–12 carbon atoms, and x is an integer (e.g., 1 or 2).

Illustrative of suitable thiol compounds are methanethiol, ethanethiol, 1-butanethiol, 1-dodecanethiol, 1,4-butanedithiol, and the like.

An important aspect of the present invention is the discovery that hindered thiol compounds exhibit superior properties in the invention thioloesterification process. For example, a tertiary thiol compound reacts with 1,3-alkadiene and carbon monoxide at an exceptionally high reaction rate and with a uniquely high selectivity to linear 3-thioloalkenoate product.

Illustrative of suitable hindered thiol compounds are secondary and tertiary thiols containing between about 3–30 carbon atoms and one or more thiolo groups, such as 2-propanethiol; 2-butanethiol; 2-methyl-2-propanethiol; 2,4-pentanedithiol; 1,1,2,2-tetramethylethanedithiol; 2-decanethiol; 3-tridecanethiol; 2-eicosanethiol; cyclohexanethiol; benzenethiol; 1,1,1-triphenylmethanethiol; and the like.

The thiol and carbon monoxide and 1,3-alkadiene coreactants can be employed in essentially any proportions as dictated by practical considerations of economy and convenience. The presence of the three coreactants per se in a reactor system satisfies the stoichiometry of the process, notwithstanding that any one coreactant may be present in molar excess relative to the other coreactants.

It is preferred that the carbon monoxide is introduced into the process reaction system up to a partial pressure of between about 300 and 2000 psi of carbon monoxide. The carbon monoxide environment in the process system can contain one or more inert gases such as nitrogen, helium, argon, and the like. For optimal results it is essential that the process is conducted in a deoxygenated environment, so as not to affect adversely the 1,3-alkadiene conversion rate and the selective yield of alkyl 3-thioloalkenoate product.

The liquid medium in the first step of the process can include a solvent diluent, in addition to the other liquid constituents in the hydroesterification reaction system. Suitable solvents include propane, butane, pentane, cyclopentane, hexane, cyclohexane, heptane, octane, tetradecane, petroleum refinery light hydrocarbon mixtures, methanol, benzene, chlorobenzene, nitrobenzene, toluene, xylene, mesitylene, tetrahydrofuran, dimethylformamide, methyl ethyl ketone, the thioloester product, and the like.

A further aspect of the present invention is the provision of a stabilized catalyst which is highly selective for thioloesterification of 1,3-alkadiene compounds. Thus, in another embodiment the present invention provides a catalyst composition consisting of a solvent solution of solute components comprising a complex of palladium and tertiary phosphine ligand which is in contact with a stabilizing quantity of thiol compound.

The "solvent" in the said stabilized catalyst composition can comprise an inert solvent diluent of the type previously described, and/or 1,3-alkadiene and/or tertiary phosphine, and the like. The said catalyst composition can be preformed prior to introduction into a thioloesterification zone, or it can be formed in situ by the separate introduction of the palladium compound, tertiary phosphine ligand and thiol components into the thioloesterification zone.

The palladium component of the catalyst composition preferably is introduced in the form of a palladium-containing compound such as palladium acetate, palladium propionate, palladium acetylacetonate, bis-(1,5-diphenyl-3-pentadienone) palladium(o), palladium nitrate, palladium sulfate, and the like. The palladium can be in either a plus two or zero valent state.

It is highly preferred that the catalyst composition is halide-free, e.g., any halide-containing salt such as palladium(II) chloride is excluded. An important advantage of a "halide-free" catalyst complex is the prevention of a highly corrosive reaction environment.

With reference to the tertiary phosphine ligand, the term "phosphine" is meant to include corresponding phosphite derivatives. Illustrative of suitable tertiary phosphine ligands are triisopropylphosphine, tri-n-butylphosphine, triisobutylphosphine, tri-n-octylphosphine, tricyclohexylphosphine, triphenylphosphine, tritolylphosphine, tribenzylphosphine, and the corresponding phosphite compounds. The substituents in the tertiary phosphine ligands can be the same or different, and mixtures of tertiary phosphine ligands can be employed. Illustrative of a ligand mixture is one containing about 70–99 mole percent trialkylphosphine (e.g., triisopropylphosphine) and about 1–30 mole percent triarylphosphine (e.g., triphenylphosphine). A preferred class of tertiary phosphine ligands are trialkylphosphines in which each alkyl group contains between 2 and about 8 carbon atoms.

It appears that a specific type of palladium/tertiary phosphine complex catalyst exhibits a superior combination of properties with respect to hydroesterification of 1,3-alkadiene in comparison with a complex of palladium and some other tertiary phosphine ligand, i.e., the preferred catalyst contains a trialkylphosphine ligand which has a ΔHNP basicity between about 70–350 and a steric parameter $\theta$ between about 136°–190°. Illustrative of this category of trialkylphosphines are triisopropylphosphine, tri-secondary-butylphosphine, triisobutylphosphine and tricyclohexylphosphine.

For example, palladium/triisopropylphosphine complex provides a better balance of conversion and selectivity as a catalyst in the present invention process than does any of palladium/tri-n-propylphosphine complex, palladium/tri-n-butylphosphine complex, palladium/diethylphenylphosphine complex, palladium/tricyclohexylphosphine complex, or palladium/triphenylphosphine complex, respectively.

By the term "ΔHNP" is meant the difference in the half neutralization potential between the ligand under consideration and N,N'-diphenylquanidine as determined in accordance with the procedure described in Analytical Chemistry, 32, 985–987 (1960). The ΔHNP of 24 tertiary phosphines are listed in U.S. Pat. No. 3,527,809.

By the term "steric parameter $\theta$" is meant the apex angle of a cylindrical cone, centered 2.28 Å from the center of the phosphorus atom, which touches the Van der Waals radii of the outermost atoms of the isopropyl substituents [C. A. Tolman, J. Amer. Chem. Soc., 92, 2953 (1970); Ibid, 92, 2956 (1970); and Ibid, 96, 53 (1974)].

It appears that the superior catalytic properties of a palladium/triisopropylphosphine type of catalyst complex are attributable to the specifically inherent basicity and steric structure of triisopropylphosphine as a complexing ligand. It is believed that the physicochemical properties of triisopropylphosphine favor the formation of a highly acitve form of complex palladium catalyst for the purposes of thioloesterification of 1,3-alkadiene compounds.

The catalyst complex of palladium salt/tertiary phosphine is provided in the hydroesterification reaction medium in at least a catalytic quantity, and the mole ratio of 1,3-alkadiene to catalyst complex preferably is at least 1:1 or higher.

The palladium and tertiary phosphine ligand in the hydroesterification zone liquid reaction medium typically are provided in a ratio between about 1–20 moles of tertiary phosphine ligand per gram atom of palladium metal.

The palladium and thiol compound in the hydroesterification zone liquid reaction medium typically are present in a ratio between about 1–100 moles of thiol compound per gram atom of palladium metal.

It is preferred to conduct the hydroesterification step of the invention process in the presence of a suitable polymerization inhibitor, e.g., hydroquinone. If an inhibitor is not included in the reaction system then there is an increased incremental loss of 1,3-alkadiene to polymeric byproducts. When a polymerization inhibitor is employed, the yield of byproducts can be limited to less than about 10 percent.

The temperature for the first step hydroesterification reaction can vary in the range between about 50° C. and 180° C. and preferably is in the range between about 80° C. and 130° C.

The pressure in the first step reaction zone can vary in the range between about 300 and 3000 psi, and preferably is in the range between about 500 and 1500 psi. As previously indicated, it is advantageous to provide a carbon monoxide partial pressure in the range between about 300 and 2000 psi in the first step reaction zone.

In a typical process, the contact time for the thioloesterification step will average in the range between about 0.5 and 50 hours, as determined by temperature and pressure parameters and the reactivity of the palladium-phosphine complex catalyst.

After the completion of the first step thioloesterification reaction, the liquid product mixture is cooled to room temperature or lower. Any high molecular weight polydiene byproducts in the reaction product mixture tend to precipitate out during the cooling stage. As necessary, the reaction product mixture can be filtered to remove polymeric precipitate.

The product mixture is then fractionated by a conventional method such as distillation to recover the alkyl 3-thioloalkenoate product. It is highly advantageous to leave some alkyl 3-thioloalkenoate as a residual solvent medium for the catalyst complex which is in solution. The said solvent solution of catalyst can be recycled to the thioloesterification step of the process.

In a batch type process, it is convenient and advantageous to perform several hydroesterification runs successively in the same reactor system, without recovery of alkyl thioloalkenoate product between the respective runs. The accumulated product is recovered after the completion of the last run.

In another embodiment, this invention contemplates a continuous process for producing and recovering alkyl thioloalkenoate. Illustrative of a specific application of the continuous process, a solution of palladium-phosphine complex is fed continuously to a first reaction zone of an elongated reactor system, simultaneously with the introduction of 1,3-alkadiene and thiol streams. In the first reaction zone, the feed materials are admixed efficiently with each other and with carbon monoxide which is present at a partial pressure of at least 300 psi (e.g., 400–700 psi). The admixture is passed into a second reaction zone of the reactor system, and the temperature and flow rates are controlled in the second reaction zone so that optimal proportions of the co-reactants are present.

A product stream is removed continuously from the end of the second reaction zone. The product stream is distilled to remove a portion of the alkyl 3-thioloalkenoate product. The residual solution of product and catalyst is recycled to the first reaction zone of the thioesterification system.

At 100° C. and 750 psi carbon monoxide pressure, tertiary-butyl 3-thiolopentenoate can be produced from 1,3-butadiene and tertiary-butylthiol with a space-time yield of about 450 grams per liter-hour, and a Linear/Branched ratio of about 300/1.

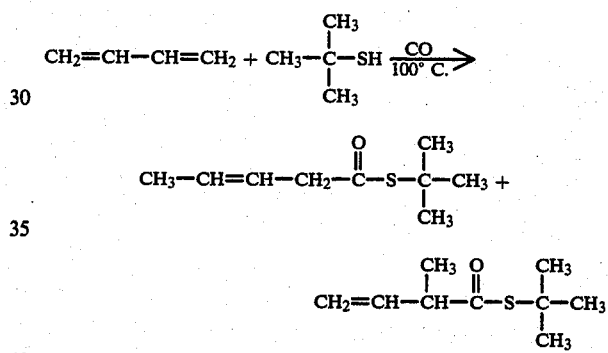

An interesting aspect of the present invention is the relative absence of dimeric thioloesterification product under the preferred reaction conditions of the invention process, e.g., only a trace amount of tertiary-butyl 3,8-thiolononadienoate is detected in the product mixture when 1,3-butadiene is thioloesterified with tertiary-butylthiol and carbon monoxide. Further, it has been observed that the production of dimeric thioloesterification product tends to increase if the proportion of thiol reactant is at a low level in the reaction zone.

The following examples are further illustrative of the present invention. The reactants and other specific ingredients are presented as being typical, and various modifications can be devised in view of the foregoing disclosure within the scope of the invention.

All catalyst solutions were prepared under prepurified nitrogen employing standard anaerobic techniques. A standard 300 cc magnedrive 316 SS autoclave from Autoclave Engineers was used for pressure reactions. Gas was fed into the autoclave from a one liter storage vessel through a pressure regulator to maintain constant autoclave pressure.

The autoclave was also equipped with two 150 ml cylinders to allow addition of liquids into the autoclave while under pressure. The autoclave was evacuated to <2 mm Hg before each experiment to collect foreign condensable materials into a −196° C. trap. The reactor and tubing were flushed with carbon monoxide before each run.

Analytical instrumentation included a Finegan 4000 mass spectrometer with 70 EV ionizing voltage; a Varian CFT-20 (80 MHz) spectrometer; and a Perkin-Elmer Model 457 grating spectrophotometer.

Reaction products were separated and isolated on a 10-foot, ⅜-inch aluminum column packed with 8% Dexil 300 on Anakrom Q 60/80 mesh (Supelco, Inc.).

As a general procedure for catalyst preparation, a nitrogen-flushed flask was sequentially charged with palladium(II) diacetate (0.9 g, 4.0 mmole), 20 ml of dry deoxygenated tetrahydrofuran (THF), triisopropylphosphine (0.8 ml, 0.7 g, $4.5 \times 10^{-3}$ mole) and 0.5 g of hydroquinone. Upon stirring the mixture at room temperature for 15 minutes, a deep red-brown solution resulted which constituted the catalyst solutions.

For experiments in which THF was not a desirable solvent, the THF was removed on a rotary evaporator at <50° C. to yield a red-brown solid. This air-stable catalyst solid was dissolved in an alternate solvent or liquid reagent before use.

In a typical thioloesterification run, a nitrogen-flushed cylinder was charged with the THF catalyst solution, thiol (about 25 ml) and tetradecane (12.5 ml, $48 \times 10^{-2}$ mole). Into an alternate cylinder was placed 1,3-butadiene (50 g). These cylinders were installed into a reactor system which were adapted for injection of these solutions into an autoclave by means of carbon monoxide pressure.

A 300 ml 316 SS magnadrive autoclave was evacuated to 0.1 torr to remove any volatile impurities, then flushed with carbon monoxide and charged at room temperature with the catalyst solution employing 100 psia of carbon monoxide. The butadiene was charged into the reactor using 500 psia of carbon monoxide.

The reactor temperature was raised to 100° C. as quickly as possible (about 0.5 hour) and stabilized at this temperature. The reactor pressure was maintained at 750 psia employing carbon monoxide fed from a one liter storage vessel.

The reaction was monitored as a function of time by observing both the change in pressure in the one liter storage vessel and the appearance of products by g.c. A 1 ml sample was taken from a bottom liquid sampling tap on the autoclave at a given time. This sampling line was washed with pentane and flushed with nitrogen after each sample was taken.

EXAMPLE I

This Example illustrates the preparation of three butyl 3-thiolopentanoate products under mild reaction conditions.

The results obtained with n-butylthiol, sec-butylthiol and t-butylthiol are listed in Table I.

The reaction was highly selective for $\beta,\gamma$-unsaturation (i.e., about 100%), with a cis/trans (or trans/cis) ratio dependent on the thiol employed.

Both sec-butylthiol and t-butylthiol gave a cis/trans (or trans/cis) ratio of about 5/1, while the ratio with n-butylthiol was about 14/1.

Minor quantities (e.g., <3%) of butyl 3,8-thiolononadienoate products were observed. The n-butanethiol reaction produced more of the diene byproduct than did the sec-butanethiol and t-butanethiol reactions, respectively. In all cases, the formation of butyl 3,8-thiolononadienoate byproduct was not observed in samples until after about 20 hours of reaction time.

Reagents and conditions for the first n-butylthiol reaction were n-butylthiol (0.119 mole), 1,3-butadiene (0.926 mole), tetradecane ($4.81 \times 10^{-2}$ mole) as a g.c. internal standard, hydroquinone (0.25 g), tetrahydrofuran (52 ml), (1:1) Pd(OAc)$_2$/iso-Pr$_3$P (4.0 mmole); and 101° C., 770 psia (CO). The liquid volume was 140 ml. No palladium metal was observed during the 25.5 hour reaction period.

Reagents and conditions for the second n-butane reaction were n-butanethiol (0.374 mole), 1,3-butadiene, tetradecane ($4.81 \times 10^{-2}$ mole), toluene (10 ml), hydroquinone (0.25 g), (1:1) bis-(1,5-diphenyl-3-pentadienenone) palladium (o)/iso-Pr$_3$ (4.0 mmole); and 107° C., 750 psia reactor pressure*. The liquid volume was 135 ml. A trace of palladium metal was observed during the 20.9 hour reaction period, after depletion of n-butanethiol.

*Vapor pressure of reagents and partial pressure of carbon monoxide.

Reagents and conditions for the sec-butylthiol reaction were sec-butylthiol (0.355 mole), tetradecane ($4.81 \times 10^{-2}$ mole), 1,3-butadiene (0.926 mole), hydroquinone (0.25 g), methanol (20 ml), (1:1) Pd(OAc)$_2$/iso-Pr$_3$P (4.0 mmole), and 99° C., 773 psia reactor pressure. The liquid volume was 146 ml, and no plating out of palladium metal was observed during the 20.8 hour reaction period.

Reagents and conditions for the t-butylthiol reaction were t-butylthiol (0.222 mole), 1,3-butadiene (0.222 mole), tetradecane ($4.81 \times 10^{-2}$ mole), hydroquinone (0.25 g), toluene (35 ml), tetrahydrofuran (5 ml), (1:1) Pd(OAc)$_2$/iso-Pr$_3$P (4.0 mmole); and 102° C., 780 psia reactor pressure. The solution volume was 97.5 ml, and no palladium metal was observed during the 4.8 hour reaction period.

Besides the results listed in Table I, it is noteworthy that the t-butyl 3-thiolopentenoate/t-butyl 2-methyl-3-thiolobutenoate ratio (i.e., Linear/Branched ratio) in the product mixture was 311/1.

TABLE I

| | | Butyl 3-thiolopentenoate | | Butyl 3,8- |
|---|---|---|---|---|
| Thiol | Catalyst[a] | STY g/l-h | Cis/Trans[b] ratio | Thiolononadienoate, %[c] |
| n-BuSH | A | 14.6 | 14.1/1 | 11.1 |
| n-BuSH | B | 19.8 | 13.4/1 | 1.4 |
| sec-BuSH | A | 14.9 | 4.9/1 | 0.4 |
| t-BuSH | A | 455.0 | 5.6/1 | <0.5 |

[a]Catalyst A: (1:1) Pd(OAc)$_2$/iso-Pr$_3$P;
Catalyst B: (1:1) bis-1,5-diphenyl-3-pentadienone palladium(o)/iso-Pr$_3$P.
[b]No certainty whether the ratio represented trans/cis or cis/trans for the unsaturation in butyl 3-thiolopentenoate.
[c]Yield is based on charged thiol.

EXAMPLE II

This Example illustrates the reaction of p-thiocresol with 1,3-butadiene in accordance with the present invention process.

The reagents and reaction conditions were p-thiocresol (0.328 mole), 1,3-butadiene (0.926 mole), tetradecane ($4.81 \times 10^{-2}$ mole), hydroquinone (0.25 g), (1:1) Pd(OAc)$_2$/iso-Pr$_3$P (4.0 mmole), methanol (5 ml), pentane (60 ml); and 101° C., 750 psia reactor pressure. The solution volume was 175 ml, and no palladium metal was observed during the 3.25 hour reaction period.

The products were identified as 1-(p-methylphenylthio)-2-butene, 1-(p-methylphenylthio)-3-butene and p-methylphenyl 3-thiolopentenoate:

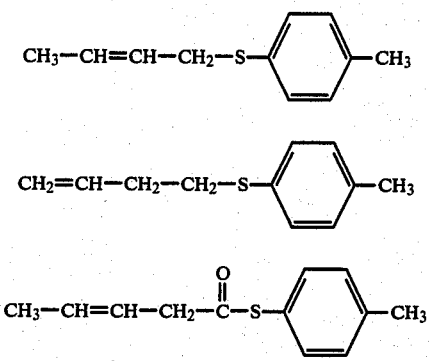

There was an STY of 8.7 g/l-h (0–50% p-thiocresol conversion) for p-thiocresol utilization, and an overall yield of 18.4% p-methylphenyl 3-thiolopentenoate and 33.2% 1-(p-methylphenylthio)-2-butene and 1-(p-methylphenylthio)-3-butene (based on p-thiocresol charged) for a 23 hour reaction period. The 2-butene/3-butene ratio was 2.45/1.

EXAMPLE III

This Example illustrates the preparation of t-butyl 3-thiolohexenoate.

The reagents and reaction conditions were 1,3-pentadiene (0.266 mole), t-butylthiol (0.266 mole), tetradecane (4.81×10$^{-2}$ mole), (1:2) Pd(OAc)$_2$/iso-Pr$_3$P (4.0 mmole), methanol (5 ml); and 94° C. and 750 psia reactor pressure. The liquid volume was 75 ml, and no palladium metal was observed during the 21.5 hour reaction period.

The reaction product consisted of a mixture of t-butyl 3-thiolohexenoate and t-butyl 2-methyl-3-thiolopentenoate in a ratio of 1.9/1. An overall STY of 220 g/l-h (for 0–50% 1,3-pentadiene) conversion was obtained. The minimum conversion of 1,3-pentadiene was 87%, and no dimerization products were detected.

The mole yields of t-butyl 3-thiolohexanoate and t-butyl 2-methyl-3-thiolopentenoate were 56.5% and 30.1%, respectively (based on the 1,3-pentadiene charged).

EXAMPLE IV

This Example illustrates the preparation of t-butyl 3-thioloheptenoate.

The reagents and conditions were 1,3-hexadiene (0.266 mole), t-butylthiol (0.266 mole), tetradecane (4.81×10$^{-2}$ mole), (1:2) Pd(OAc)$_2$/iso-Pr$_3$P (4.0 mmole), tetrahydrofuran (20 ml); and 100° C., 750 psia reactor pressure. The liquid volume was 90.5 ml, and no plating out of palladium was observed during the 21.3 hour reaction period.

The reaction product consisted of a mixture of t-butyl 3-thioloheptenoate and t-butyl 2-methyl-3-thiolohexenoate/t-butyl 2-methyl-4-thiolohexenoate. The STY was calculated to be 293.9 g/l-h (for 0–50% 1,3-hexadiene conversion). The three products accounted for 84.3% of the 1,3-hexadiene charged, and no dimerization products were detected.

The mole yields of t-butyl 3-thioloheptenoate, and a mixture of t-butyl 2-methyl-3-thiolohexenoate and t-butyl 2-methyl-4-thiolohexenoate were 61.2% and 23.1%, respectively, based on the 1,3-hexadiene charged.

What is claimed is:

1. A process for monomeric thioloesterification of 1,3-alkadiene which comprises (1) reacting 1,3-alkadiene with carbon monoxide and thiol compound in a liquid medium containing a stabilized halide-free catalyst complex of palladium and tertiary phosphine ligand; and (2) recovering alkyl 3-thioloalkenoate product.

2. A process in accordance with claim 1 wherein the 1,3-alkadiene reactant in step(1) is an acyclic or cyclic 1,3-alkadiene containing between about 4–20 carbon atoms.

3. A process in accordance with claim 1 wherein the thiol compound in step(1) is a primary, secondary or tertiary thiol containing between about 1–12 carbon atoms and 1–2 thiol groups.

4. A process in accordance with claim 1 wherein the liquid medium in step(1) comprises an organic solvent solution of reactants and catalyst complex.

5. A process in accordance with claim 1 wherein the catalyst complex in step(1) is provided in at least a catalytic quantity, and the mole ratio of 1,3-alkadiene to catalyst complex is at least 1:1 or higher.

6. A process in accordance with claim 1 wherein the palladium and tertiary phosphine ligand in the step(1) liquid medium are in a ratio between about 1–20 moles of tertiary phosphine ligand per gram atom of palladium metal.

7. A process in accordance with claim 1 wherein the step(1) reaction is conducted at a temperature between about 50°–180° C. for a contact time between about 0.5–50 hours.

8. A process in accordance with claim 1 wherein the step(1) reaction is conducted at a pressure between about 300–3000 psi.

9. A process in accordance with claim 1 wherein the 1,3-alkadiene reactant in step(1) is 1,3-butadiene and the recovered product in step(2) is alkyl 3-thiolopentenoate.

10. A process in accordance with claim 1 wherein the 1,3-alkadiene reactant in step(1) is 2-methyl-1,3-butadiene.

11. A process in accordance with claim 1 wherein the 1,3-alkadiene reactant in step(1) is 1,3-pentadiene or 1,3-cyclopentadiene.

12. A process in accordance with claim 1 wherein the 1,3-alkadiene reactant in step(1) is 1,3-hexadiene or 1,3-cyclohexadiene.

13. A process in accordance with claim 1 wherein the thiol compound in step(1) is 1-butanethiol.

14. A process in accordance with claim 1 wherein the thiol compound in step(1) is 2-butanethiol.

15. A process in accordance with claim 1 wherein the thiol compound in step(1) is 2-methyl-2-propanethiol.

16. A process in accordance with claim 1 wherein the thiol compound in step(1) is p-thiocresol.

17. A process in accordance with claim 1 wherein the thiol compound in step(1) is 1-dodecanethiol.

18. A process in accordance with claim 1 wherein the thiol compound in step(1) is 1,4-butanedithiol.

19. A process in accordance with claim 1 wherein the step(1) catalyst is a stabilized complex of palladium, tertiary phosphine ligand and thiol compound.

20. A process in accordance with claim 1 wherein the palladium in the step(1) catalyst complex is palladium diacetate 21. A process in accordance with claim 1 wherein the palladium in the step(1) catalyst complex is in the form of zero valent palladium.

22. A process in accordance with claim 1 wherein the tertiary phosphine ligand in the step(1) catalyst complex is trialkylphosphine.

23. A process in accordance with claim 1 wherein the tertiary phosphine ligand in the step(1) catalyst complex is triisopropylphosphine.

24. A process in accordance with claim 1 wherein the tertiary phosphine ligand in the step(1) catalyst complex is tri-n-butylphosphine.

25. A process in accordance with claim 1 wherein the tertiary phosphine ligand in the step(1) catalyst complex is tri-secondary-butylphosphine or tri-cyclohexylphosphine.

26. A process in accordance with claim 1 wherein the tertiary phosphine ligand in the step(1) catalyst complex is a mixture of tertiary phosphines.

27. A process in accordance with claim 1 wherein a polymerization inhibitor is present in the step(1) liquid medium.

28. A process in accordance with claim 1 wherein a liquid fraction containing stabilized catalyst complex is recovered in step(2) and recycled to step(1).

* * * * *